(12) United States Patent
Forde et al.

(10) Patent No.: US 11,529,041 B2
(45) Date of Patent: Dec. 20, 2022

(54) DEVICES AND METHODS FOR GUIDING INSTRUMENTS

(71) Applicant: CSA Medical, Inc., Lexington, MA (US)

(72) Inventors: Sean Forde, Watertown, MA (US); Brian M. Hanley, Reading, MA (US); Sean A. McDermott, Weymouth, MA (US)

(73) Assignee: CSA Medical, Inc., Lexington, MA (US)

( * ) Notice: Subject to any disclaimer, the term of this patent is extended or adjusted under 35 U.S.C. 154(b) by 900 days.

(21) Appl. No.: 16/279,555

(22) Filed: Feb. 19, 2019

(65) Prior Publication Data

US 2019/0254699 A1 Aug. 22, 2019

Related U.S. Application Data

(60) Provisional application No. 62/633,123, filed on Feb. 21, 2018.

(51) Int. Cl.
| | | |
|---|---|---|
| *A61B 1/00* | (2006.01) | |
| *A61B 18/02* | (2006.01) | |
| *A61B 17/34* | (2006.01) | |
| *A61M 16/04* | (2006.01) | |
| *A61M 25/00* | (2006.01) | |
| *A61B 17/00* | (2006.01) | |

(52) U.S. Cl.
CPC ............ *A61B 1/00135* (2013.01); *A61B 1/00* (2013.01); *A61B 17/3431* (2013.01); *A61B 18/0218* (2013.01); *A61M 16/049* (2014.02); *A61M 16/0497* (2013.01); *A61B 17/3415* (2013.01); *A61B 2017/00336* (2013.01); *A61B 2017/00477* (2013.01); *A61B 2017/00858* (2013.01); *A61B 2018/0212* (2013.01); *A61M 25/005* (2013.01)

(58) Field of Classification Search
CPC ........ A61M 2025/0025; A61M 25/005; A61B 1/00135; A61B 1/0014; A61B 17/3431
See application file for complete search history.

(56) References Cited

U.S. PATENT DOCUMENTS

| | | | | |
|---|---|---|---|---|
| 5,472,418 A | * | 12/1995 | Palestrant | A61M 25/0023 604/523 |
| 6,663,591 B1 | * | 12/2003 | d'Ussel | A61M 5/50 604/110 |
| 8,696,550 B2 | * | 4/2014 | Surti | A61B 1/012 600/114 |
| 2003/0120208 A1 | * | 6/2003 | Houser | A61M 25/104 604/103.04 |
| 2005/0107819 A1 | * | 5/2005 | Sater | A61M 25/00 604/528 |
| 2005/0171470 A1 | * | 8/2005 | Kucklick | A61M 25/0662 604/263 |

(Continued)

*Primary Examiner* — William R Carpenter
(74) *Attorney, Agent, or Firm* — Goodwin Procter LLP

(57) ABSTRACT

The present disclosure relates generally to the field of medical devices. In particular, the present disclosure relates to devices and methods to guide delivery devices and instruments. Exemplary instrument guides, including for endoscopes as delivery devices for cryogen delivery catheters and to guide cryogen decompression tubes as instruments, and methods for use of such instrument guides for use in body lumens at treatment sites, are disclosed.

10 Claims, 7 Drawing Sheets

(56) References Cited

U.S. PATENT DOCUMENTS

| | | | |
|---|---|---|---|
| 2006/0270978 A1* | 11/2006 | Binmoeller | A61B 1/00154 |
| | | | 604/104 |
| 2007/0088319 A1* | 4/2007 | Martone | A61M 25/0662 |
| | | | 606/108 |
| 2008/0125752 A1* | 5/2008 | Gunderson | A61M 25/0012 |
| | | | 604/524 |
| 2008/0154352 A1* | 6/2008 | Goshgarian | B29C 33/42 |
| | | | 623/1.11 |

* cited by examiner

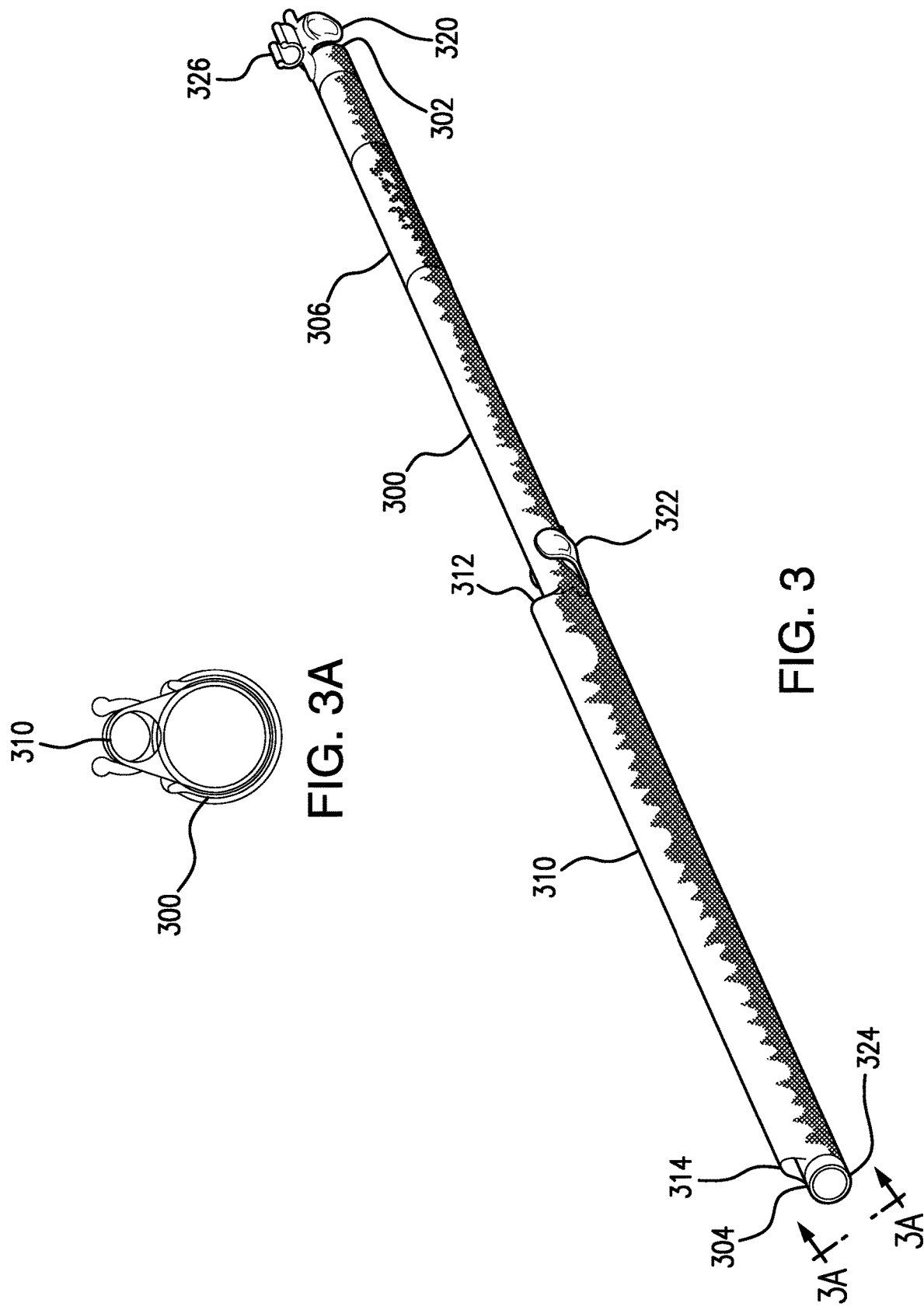

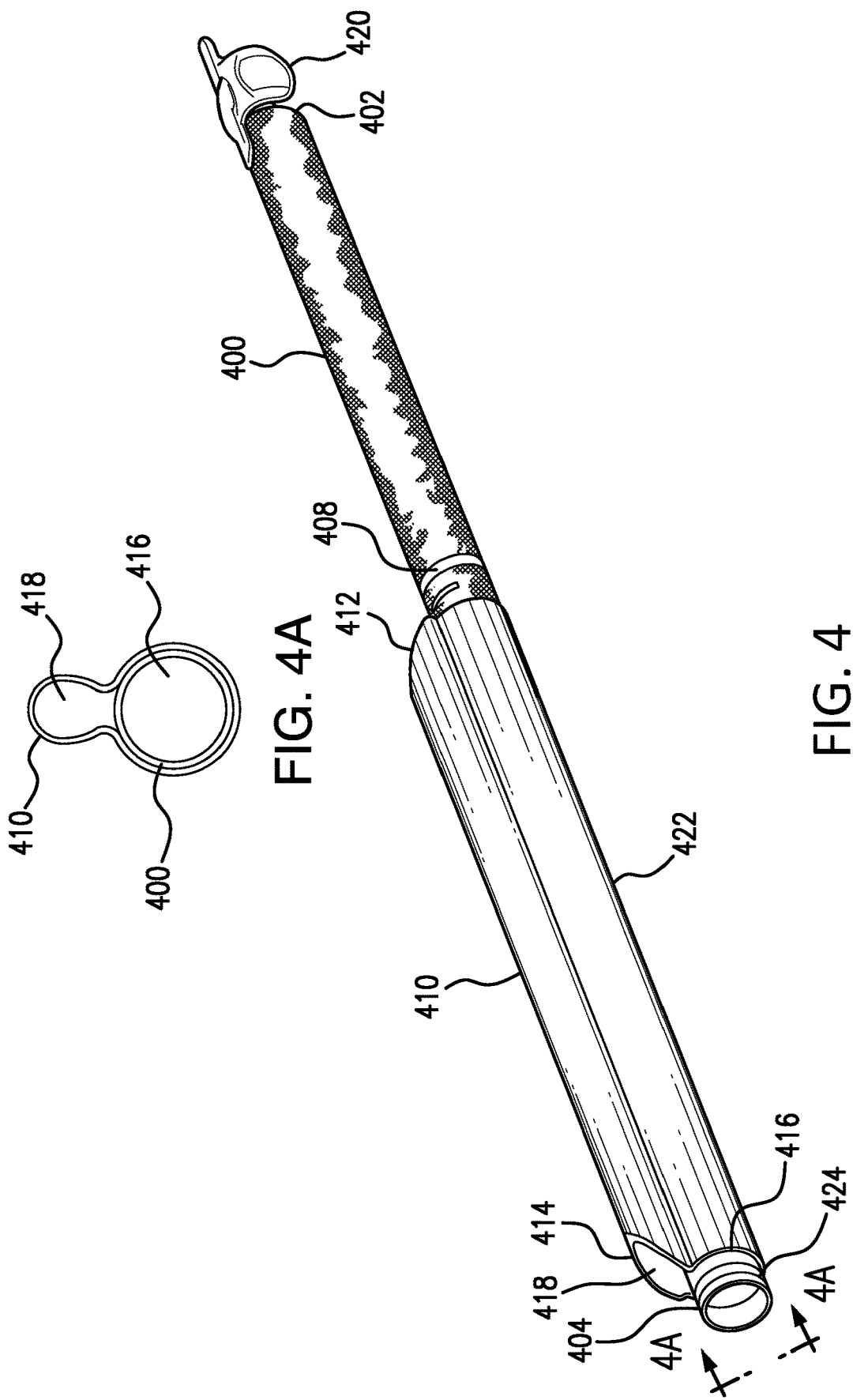

DEVICES AND METHODS FOR GUIDING INSTRUMENTS

PRIORITY

This application claims the benefit of priority under 35 USC § 119 to U.S. Provisional Patent Application Ser. No. 62/633,123, filed Feb. 21, 2018, which is incorporated by reference herein in its entirety and for all purposes.

FIELD

The present disclosure relates generally to the field of medical devices. In particular, the present disclosure relates to devices and methods for delivery devices to guide instruments. Exemplary instrument guides, including for endoscopes as delivery devices for cryogen delivery catheters and to guide cryogen decompression tubes as instruments, and methods for use of such instrument guides in body lumens at treatment sites, are disclosed.

BACKGROUND

Delivery devices, such as endoscopes, for transporting medical devices into the body (e.g., a device having a working channel extending therethrough that is configured to slidingly receive a catheter) and for performing procedures in the body at treatment sites along with other instruments necessary to the procedures, exist in various forms, for different applications, and across a range of treatment sites. In endoscopic procedures, frequently medical instruments need to be introduced into the body outside of the working channel of an endoscope. For example, during spray cryotherapy, a cryo-decompression tube (CDT), gas removal tube (GRT), or gas egress tube (GET) must be placed into the stomach before treating the esophagus in order to evacuate cryogen gas that is generated during the treatment. As the tube is not attached to any other device, it typically lays on the surface of the body lumen, which may create an untreated area behind the CDT during the therapy if the CDT masks the cryospray, preventing the masked tissue from fully freezing. The clinician must remove and reorient the tube in a different position to treat the untreated area or return for a second procedure. As such tubes or other instruments may be placed over a guidewire, guidewires present an additional potential object in the working channel of the endoscope or at the treatment site, or both.

It is with respect to these considerations that the devices, systems and methods of the present disclosure for an instrument guide may be useful.

SUMMARY

The present disclosure in its various embodiments includes devices and methods of use for instrument guides that may be used to more efficiently manage delivery devices and instruments to provide, among other benefits, a more productive work space at treatment sites. Various embodiments act as an external working channel to allow instruments to extend along a delivery device, the radial and longitudinal position of which may be better controlled by a medical professional.

In various embodiments of the present disclosure, an instrument guide may include a collapsible elongate braid with a proximal end opening, a distal end opening, and a lumen extending therebetween configured to slidingly receive a delivery device. An instrument guide may include a collapsible instrument braid with a proximal end opening, a distal end opening, and a lumen extending therebetween configured to slidingly receive an instrument. The instrument braid lumen may extend substantially parallel to the elongate braid lumen. The instrument braid may be braided with the elongate braid. The delivery device may be an endoscope or a catheter. The delivery device may be a bronchoscope having a working channel extending therethrough that is configured to slidingly receive a cryogen delivery catheter. A coating may be disposed within the lumen of the elongate braid adjacent to the instrument braid. The coating may have a higher coefficient of friction than the elongate braid. The coating may be a thermoplastic elastomer. The coating may be disposed proximal to the proximal end opening of the instrument braid and may be distal to the distal end opening of the instrument braid. The coating may form a strip that is disposed about the elongate braid in a helical manner. A proximal end portion of the elongate braid and a distal end portion of the elongate braid may be coated with a thermoplastic elastomer. An instrument guide may include reinforcing braided rings disposed at and extending around each of the proximal end openings and the distal end openings of the instrument braid and the elongate braid. The rings may be braided with the proximal end opening and the distal end opening. The lumens of the elongate braid and instrument braid may be collapsible independent of each other. The lumen of the instrument braid may be collapsible about an outer surface of the elongate braid when there is a delivery device disposed within the lumen of the elongate braid. The instrument braid may have a length and may be disposed proximal to the distal end opening and distal to the proximal end opening of the elongate braid. The length of the instrument braid may be less than half of a length of the elongate braid. The length of the instrument braid may be about 50 millimeters. A diameter of the lumen of the instrument braid with an instrument received therein may be less than or equal to a diameter of the lumen of the elongate braid with a delivery device received therein.

In various embodiments of the present disclosure, an instrument guide may include a clip distal to the proximal end opening of an elongate braid that is configured to axially and rotationally fix the instrument guide with respect to a delivery device received within the elongate braid. A clip may have a channel substantially parallel to a lumen of the elongate braid. The channel may be configured to fixedly receive an instrument. The channel may be aligned longitudinally with the lumen of the instrument braid. The channel may be located at a terminal end of an extension arm of a clip that extends radially away from the lumen of the elongate braid and may be substantially parallel with the lumen of the instrument braid. The lumen of the instrument braid may be configured to slidingly receive a cryogen decompression tube (CDT) or gas egress tube (GET). An instrument guide may include marking bands disposed on the elongate braid. The elongate braid may have a length and a midpoint along the length. The instrument braid may have a length with the proximal end opening of the instrument braid beginning at substantially the midpoint of the elongate braid and extending along the lengths of the elongate braid and instrument braid to the distal end opening of the instrument braid coterminous with the distal end opening of the elongate braid.

In various embodiments, an instrument guide may include a first clip having a substantially C-shaped channel disposed about a lumen of an elongate braid at a proximal end opening of a lumen of an instrument braid, and a second clip having a substantially C-shaped channel disposed about the lumen of the elongate braid at the distal end opening of the lumen of the instrument braid. An instrument guide may have a third clip having a substantially C-shaped channel disposed about the lumen of the elongate braid at the proximal end opening of the elongate braid. The first clip and the third clip may engage the lumen of the elongate braid about 180 degrees opposed to each other. The distal and proximal end openings of the lumen of the instrument braid may be sloped. The elongate braid may be configured to slidingly receive a delivery device longitudinally along the lumen of the elongate braid. An instrument guide may include a transitional braid band that is circumferential about the elongate braid, separating a distal portion of the elongate braid from a mid-portion of the elongate braid. A diameter of the lumen of an instrument braid when an instrument is received therein may range from about 5% to about 100% of a diameter of the lumen of an elongate braid when a delivery device is received therein. An elongate braid and an instrument braid may comprise a braid of woven or knitted polymeric or metallic material.

In various embodiments, an instrument guide system may include an endoscope. A system may include a cryogen delivery catheter disposed within the endoscope. A system may include an external guide disposed about the endoscope. A system may include one or more instruments disposed within the external guide. The external guide may include a braided delivery device lumen disposed about the endoscope and a braided instrument lumen for the one or more instruments disposed therein.

In various embodiments, an instrument guide may include a collapsible elongate braid with a proximal end opening, a distal end opening, and a lumen extending therebetween configured to receive a delivery device. An elongate member may be disposed around a distal portion of the elongate braid that includes the distal end opening. The elongate member may have a proximal end, a distal end, and a lumen extending therebetween. The lumen of the elongate member may have a delivery device portion and an instrument portion. The instrument portion may have a sloped opening at the proximal end and the distal end of the elongate member. The delivery device may be an endoscope. The delivery device portion may be configured to receive the endoscope. The instrument portion may be configured to receive an instrument. The elongate member may be rigid. The instrument portion may have a diameter that is smaller than a diameter of the delivery device portion. The delivery device portion may be coaxial with the elongate braid and may be configured to receive the elongate braid within the delivery device portion of the elongate member lumen. An instrument guide may include a reinforcing ring that may extend distally from the delivery device portion and may be substantially coaxial with the delivery device portion. An instrument guide may include a clip proximate to the proximal end opening of the elongate braid. The clip may be configured to rotationally fix the instrument guide to a delivery device. The clip may have a channel substantially parallel to the lumen of the elongate braid. The channel may be configured to fixedly receive an instrument. The channel may be aligned longitudinally with the lumen of the instrument braid. The channel may be located at a terminal end of an extension arm of the clip that extends radially away from the lumen of the elongate braid and may be substantially parallel with the lumen of the instrument braid.

In various embodiments, an instrument guide system may include a mouthpiece. A system may include an accessory device for an external guide that is attachable to the mouthpiece. The accessory device may include a base extending between a first end and a second end of the base. The base may be configured to span a depth of the mouthpiece. A first connection element at the first end may be configured to connect to the mouthpiece. A second connection element may be at the second end substantially opposing the first connection element and may be configured to connect to the mouthpiece. An arm may extend away from the base to a terminal clip end. A clip may be at the terminal clip end having a channel along a longitudinal axis that may be substantially perpendicular to an airway path of the mouthpiece and may be configured to fixedly receive one or more instruments disposed within a braided instrument lumen of the external guide. The arm may curve away from the airway path from the base to the terminal clip end. The clip may be substantially C-shaped. The clip may be configured to fixedly receive the one or more instruments with respect to the external guide and independent of relative translation of a cryogen delivery catheter.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 3 and 3A illustrate a perspective and end cross-section view of an instrument guide in accordance with an embodiment of the present disclosure.

FIGS. 4 and 4A illustrate a perspective and end cross-section view of an instrument guide in accordance with an embodiment of the present disclosure.

DETAILED DESCRIPTION

Figure 1:
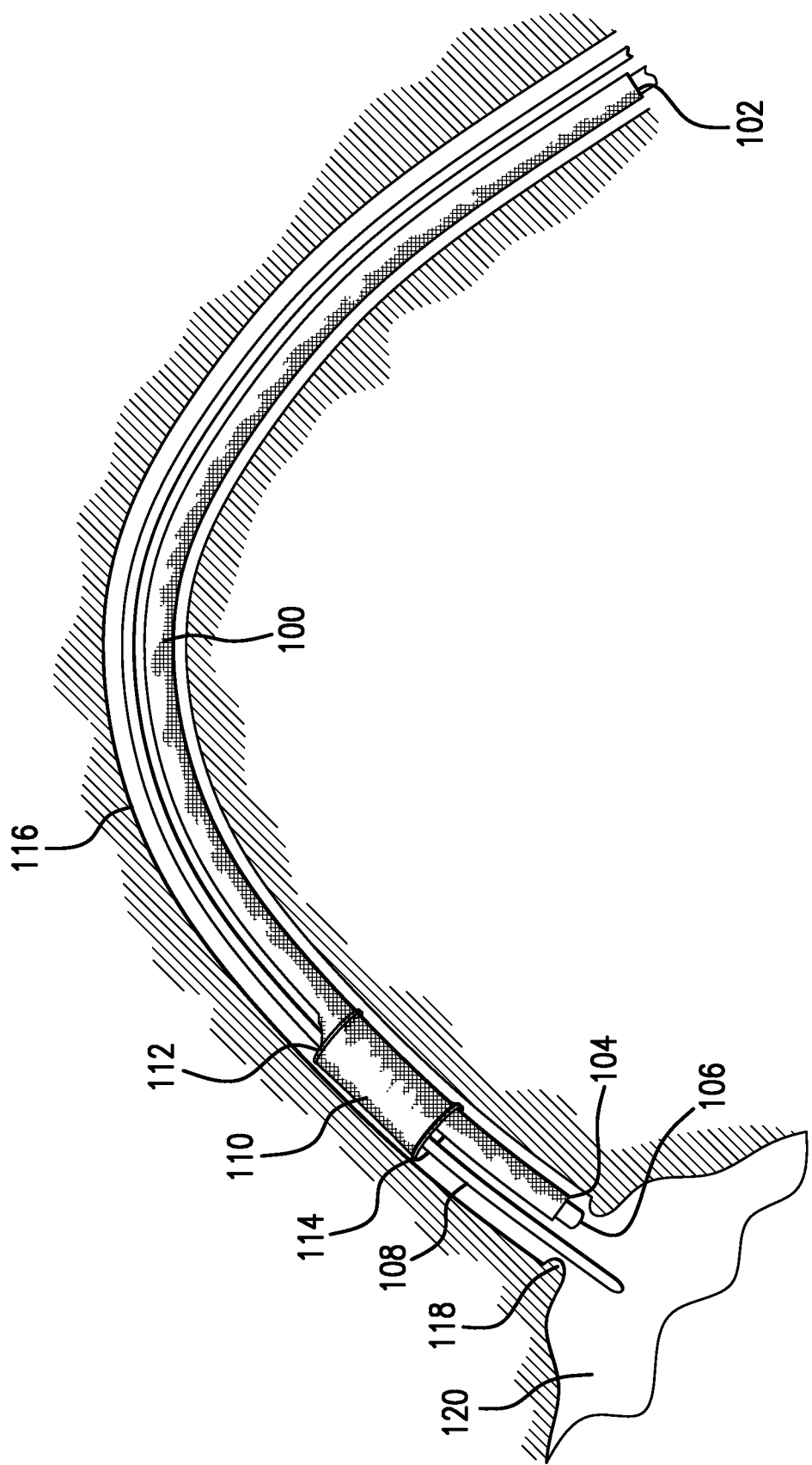
FIG. 1 illustrates an instrument guide system with an instrument guide, and a delivery device and an instrument within the instrument guide, in a body lumen, in accordance with an embodiment of the present disclosure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs. Although embodiments of the present disclosure are described with specific reference to instrument guides and systems, and methods for their use, to endoscopically deliver cryospray systems for use within the upper and lower GI tracts and respiratory system, it should be appreciated that such devices, systems and methods may be used in a variety of other body passageways, organs and/or cavities, such as the vascular system, urogenital system, lymphatic system, neurological system, and the like, and with respect to a variety of other delivery devices and instruments.

As used herein, the singular forms "a," "an," and "the" are intended to include the plural forms as well, unless the context clearly indicates otherwise. It will be further understood that the terms "comprises" and/or "comprising," or "includes" and/or "including," or "has" and/or "having" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

As used herein, the term "distal" refers to the end farthest away from the medical professional when introducing a device into a patient, while the term "proximal" refers to the end closest to the medical professional when introducing a device into a patient. As used herein, "diameter" refers to the distance of a straight line extending between two points and does not necessarily indicate a particular shape.

The present disclosure in its various embodiments provides devices and methods to guide instruments. The instrument guides, systems and methods for guiding instruments along with and in proximity to delivery devices for use in body lumens may be used to more efficiently manage the delivery devices and instruments to provide, among other benefits, a more productive work space at treatment sites in the body lumens.

For example, various embodiments of instrument guides and systems, within the scope of the present disclosure, may be used with delivery devices and instruments typical of cryosurgery systems, including cryospray systems or spray cryotherapy systems. Exemplary cryosurgery systems, including the delivery devices and instruments for use therewith, in which the present disclosure may be implemented include, but are not limited to, those systems described in U.S. Pat. Nos. 9,820,797, 9,301,796 and 9,144,449, and U.S. patent application Ser. No. 14/012,320, each of which are herein incorporated by reference in their entirety.

Various embodiments of the present disclosure allow for a variety of endoscopic instruments (e.g. a CDT, biopsy devices, stent sizers and stent delivery systems) to extend alongside a delivery device such as an endoscope during insertion and while the endoscope remains inserted into a body lumen or other anatomy, the radial and longitudinal position, and orientation, of which may be better controlled by a user with respect to the instrument guide, the delivery device, or a device within the delivery device, or some combination thereof. Once the delivery device within the instrument guide is advanced to a desirable location in the body lumen, the instruments may be freely advanced (axially/longitudinally), and/or fixed in position, relative to or independently of the instrument guide, the delivery device and/or one or more devices inserted through the delivery device, such as a cyrogen delivery catheter through the working channel of an endoscope. An instrument braid of the instrument guide may slidingly receive an instrument. The instrument braid may be an external guide from the delivery device. Various embodiments allow for rotation and management of the instrument during the procedure. A delivery device may include, e.g., an endoscope, a bronchoscope, a catheter, or the like.

Various embodiments may include one or more clips. One or more clips may be configured to axially and rotationally fix an instrument guide with respect to a delivery device received within an elongate braid. A clip may be disposed about a lumen of the elongate braid. A clip may have a channel substantially parallel to a lumen of an elongate braid. A channel may be configured to fixedly receive an instrument. A channel of a clip may be located at a terminal end of an extension arm of the clip that extends radially away from the lumen of the elongate braid and is substantially parallel with the lumen of an instrument braid.

In one embodiment of an instrument guide system for a delivery device and one or more instruments, as illustrated in FIG. 1, an instrument guide includes a collapsible elongate braid 100 having a proximal end opening 102, a distal end opening 104, and a lumen extending therebetween. The lumen of the collapsible elongate braid is configured to slidingly receive a delivery device 106. A collapsible instrument braid 110 of the instrument guide has a proximal end opening 112, a distal end opening 114, and a lumen extending therebetween. The lumen of the instrument braid 110 extends substantially parallel to the lumen of the elongate braid 100. The instrument braid 110 is configured to slidingly receive an instrument 108.

The system with an instrument guide 110, a delivery device 106, and an instrument 108 are shown within a body lumen 116. For example, in FIG. 1, the body lumen 116 is an esophagus. The delivery device 106 is extended distally towards the gastroesophageal sphincter 118. The instrument 108 extends distally past the gastroesophageal sphincter 118 into the stomach 120. The instrument 108 and the delivery device are kept substantially parallel to each other by the instrument braid 110 and the elongate braid 100 of the instrument guide, respectively. The instrument 108 may be, e.g., a cryo decompression tube, a gas removal tube, a biopsy device, a stent sizer, a stent delivery system, and/or any other instrument suitable for use with the delivery device, such as endoscopic instruments for use with an endoscope.

The collapsible instrument braid 110 may be loaded with a delivery device 106 and an instrument 108 prior to insertion into a body lumen 116. The instrument braid 110 is substantially parallel with the collapsible elongate braid 100. The instrument braid 110 has a sloped proximal end opening 112 and a ringed distal opening 114. The instrument guide, delivery device 106 extending through the elongate braid 100, and instrument 108 extending through the instrument braid 110 may be inserted into the body lumen 116 together. The delivery device 106 may be inserted into the elongate braid 100 through the proximal end opening 102 and out of the distal end opening 104. The instrument 108 may be inserted into the instrument braid 110 through the proximal end opening 112 and out of the distal end opening 114. The elongate braid 100 may be configured to slidingly accept or receive the delivery device 106 longitudinally along the lumen of the elongate braid 100. The instrument braid 110 may be configured to slidingly accept or receive one or more instruments 108 longitudinally along the lumen of the instrument braid 110. The instrument guide may be configured to fix the position of the instrument 108 within the instrument braid 110 once a desired location is reached, such that undesired distal or proximal translation with respect to the delivery device 106 and/or a device within the delivery device 106, such as a cryogen catheter, does not occur. As contained within the instrument guide, the instrument 108 is not laying against the tissue of the body lumen 116 so as to block the tissue from treatment, e.g., from a device being delivered in the delivery device 106. The instrument guide, delivery device 106, and instrument 108 may be rotated together such that the delivery device 106 may access portions of the body lumen 116 that the instrument 108 may previously have obstructed from the delivery device 106. The instrument 108 may be advanced distally or retracted proximally with respect to the instrument braid 110 by a medical professional, e.g., anchoring the position of the instrument guide while translating the instrument 108 (e.g., holding the instrument guide and delivery device 106 in one hand while translating the instrument 108 with the other hand). The instrument guide may be rotated, allowing the instrument braid 110 to revolve the instrument 108 about the delivery device 106. The delivery device 106 may also rotate with the instrument guide or it may maintain its radial orientation about a longitudinal axis of the delivery device 106. The instrument 108 may be positioned within body lumen 116 without the use of a guidewire. However, should an instrument be typically inserted over a guidewire, e.g., to locate the instrument within challenging structure, or, e.g., in case the instrument is advanced to within the instrument braid after the instrument is already within the body, or for some other purpose, a guidewire may still be compatible. The elongate braid 100 may be about 49.5 cm. The distal end of the elongate braid 100 may be positioned about 0 cm to about 10 cm from the distal end of a scope received within the elongate braid 100 during a procedure. The instrument braid 110 may be located along a distal portion of the elongate braid 100. The instrument braid 110 may be located at a location at about 10% along the length of the elongate braid 100 from the distal end 104 to about 50% along the length of the elongate braid 100 from the distal end 104. The proximal end opening 102 and distal end opening 104 may have reinforcing braided rings that initiate and terminate the length of the elongate braid 100. The reinforcing braided rings may be disposed at and extend around each of the proximal end openings 102 and 112 and the distal end openings 104 and 114 of the elongate braid 100 and the instrument braid 110.

Figure 2:
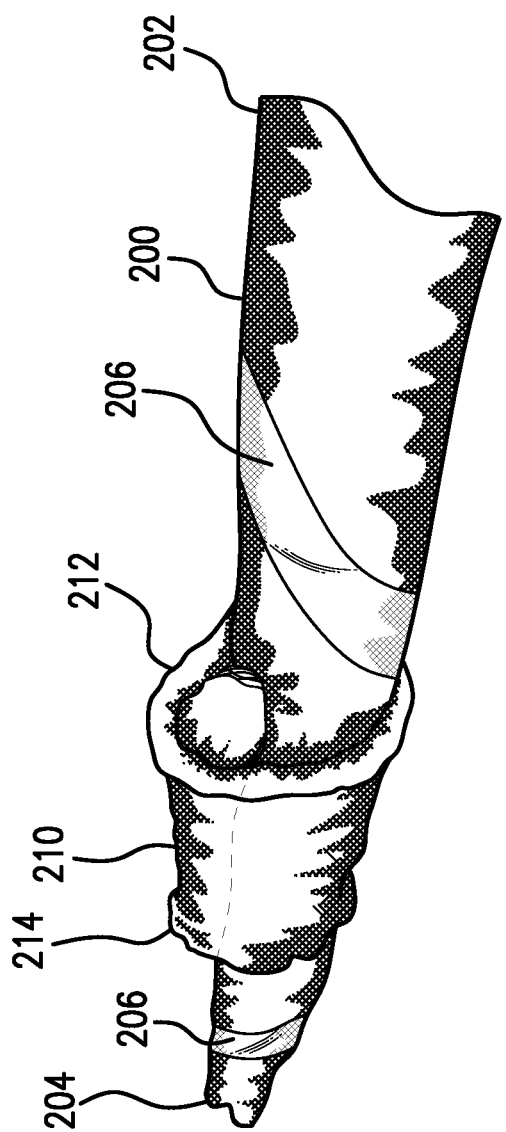
FIG. 2 illustrates a perspective view of an instrument guide in accordance with an embodiment of the present disclosure.

In one embodiment of an instrument guide for a delivery device, as illustrated in FIG. 2, a collapsible elongate braid 200 has a proximal end opening 202, a distal end opening 204, and a lumen extending therebetween. The elongate braid 200 is configured to slidingly receive a delivery device longitudinally along the lumen of the elongate braid 200. A collapsible instrument braid 210 has a proximal end opening 212, a distal end opening 214, and a lumen extending therebetween. The instrument braid 210 may be braided with the elongate braid 200. The elongate braid 200 has a length and a midpoint along the length. The instrument braid 210 extends substantially parallel to the elongate braid lumen. The instrument braid 210 may be braided with the elongate braid 200 at least by braided rings disposed at and extending around each of the proximal end opening 212 and the distal end opening 214 of the instrument braid and the elongate braid 200. The proximal end opening 212 of the instrument braid 210 may begin at substantially the midpoint of the elongate braid 200 and extend along the lengths of the elongate braid 200 and instrument braid 210 to the distal end opening 214 of the instrument braid 210 coterminous with the distal end opening 204 of the elongate braid 200. The instrument braid 210 may be a braided or knitted metallic or polymeric material, and may be a heat formed braid, a co-extruded plastic, an independent structure, or the like, attached to the elongate braid 200. The instrument braid 210 may be disposed proximal to the distal end opening 204 of the elongate braid 200 and may have a length that is about 5 to 10 cm, and up to about 100% of the entire length of the elongate braid 200 that is proximal from the distal end opening 214. The instrument guide 210 may be comprised of a thin-walled flexible material. The material of the instrument braid 210 may have a lower friction relative to that of the elongate braid 200, so as to allow axial advancement and/or retraction of an instrument through the lumen. A diameter of the lumen of the instrument braid 210 may be less than or equal to a diameter of the elongate braid 200. A diameter of the lumen of the instrument braid 210 may be about 5% to about 100% of a diameter of the lumen of the elongate braid 200, as needed to accommodate any instruments expected to be placed within the instrument braid, and within the limits of any body lumen that the instrument guide may be used inside of. A diameter of the lumen of the instrument braid 210 may accommodate instruments of up to about 16 French. The elongate braid 200 and/or the instrument braid 210 may be collapsible either independently of each other and/or collapsible together. This may allow the instrument guide to have a reduced profile while passing through a lumen of a body and/or to have a flexibility that is similar to a delivery device and/or device that is inserted through the working channel of a delivery while within the instrument, such as a flexible cryocatheter within the working channel of a flexible endoscope. Should the lumen of the elongate braid 200 be occupied with a delivery device and the lumen of the instrument braid 210 be vacant, the instrument braid 210 may collapse against and/or about the elongate braid 200. Similar locations, materials, and braids may be used with other embodiments described herein and otherwise within the scope of the disclosure.

A coating 206 may be disposed within and/or about the lumen of the elongate braid 200 and adjacent to the collapsible instrument braid 210. For example, the coating 206 may be disposed both proximally and distally from the instrument braid 210. The coating 206 may form a strip or a band that may be disposed in a helical pattern. The coating 206 may be disposed on the inside of the elongate braid 200, or the outside of the elongate braid 200, or both. The coating 206 may have a higher friction coefficient than that of the elongate braid 200. The coating 206 may be of any suitable material, such as a thermoplastic elastomer. The coating 206 may allow a delivery device to be translated through the lumen of the elongate braid 200, but still provide some traction with the delivery device within the lumen of the elongate braid 200. For example, during rotation/torsion of the delivery device and/or the elongate braid 200, the coating 206 may keep the instrument braid 210 and at least a portion of the elongate braid 200 in substantially the same radial position with respect to the delivery device. It should be appreciated that the coating 206 may allow a medical professional to rotate and/or translate the delivery device within a body lumen without the elongate braid 200 slipping at least in the areas in proximity to the coating 206. Similar coatings, locations, materials, and braids may be used with other embodiments described herein and otherwise within the scope of the disclosure In one embodiment of an instrument guide for a delivery device, as illustrated in FIG. 3, a collapsible elongate braid 300 has a proximal end opening 302, a distal end opening 304, and a lumen extending therebetween. A collapsible instrument braid 310 has a proximal end opening 312, a distal end opening 314, and a lumen extending therebetween. The instrument braid 310 extends substantially parallel to the delivery device lumen. The instrument braid 310 has a length with the proximal end opening 312 beginning at substantially a midpoint of the elongate braid 300 and extending along the lengths of the elongate braid 300 and instrument braid 310 to the distal end opening of the instrument braid 314 at the distal end opening of the elongate braid 304.

A first clip 320 at the proximal end opening 302 of the collapsible elongate braid 300 is configured to secure a wall of the elongate braid 300 against a delivery device. The first clip 320 may have a substantially C-shaped channel disposed about the lumen of the elongate braid 300 at the proximal end opening 302. A second clip 322 may have a substantially C-shaped channel disposed about the lumen of the elongate braid 300 at the proximal end opening 312 of the lumen of the instrument braid 310. The first clip 320 may engage the lumen of the elongate braid 300 about 180 degrees opposed to the second clip 322. A ring 324 may be disposed about the elongate braid 300 at the distal end 304. The ring 324 may hold the distal end of the elongate braid 300 to the delivery device. The first clip 320 has an extension arm that extends radially away from the lumen of the elongate braid 300 and has a channel 326 substantially parallel to the lumen of the elongate braid 300. The channel 326 is configured to fixedly receive an instrument, substantially preventing the instrument from sliding axially in a distal or proximal direction with respect to the instrument guide. The channel 326 may be aligned longitudinally with the lumen of the instrument braid 300 and/or the channel 326 may be parallel with the lumen of the instrument braid 310. A coating 306 may be disposed within the lumen of the elongate braid 300 that may have traction with a delivery device within the lumen of the elongate braid 300. During rotation/torsion of the delivery device and/or the elongate braid 300, the coating 306 may keep the instrument braid 310 and at least a portion of the elongate braid 300 in substantially the same radial position with respect to the delivery device.

In one embodiment of an instrument guide for a delivery device, as illustrated in FIG. 4, a collapsible elongate braid 400 has a proximal end opening 402, a distal end opening 404, and a lumen extending therebetween. An elongate member 410 is disposed around the distal end of the elongate braid 400. The elongate member 410 may be rigid. The elongate member 410 has a proximal end 412, a distal end 414, and a lumen extending therebetween. The lumen has a delivery device portion 416 and an instrument portion 418. The instrument portion 418 may have a tapered and/or sloped opening at the proximal end 412 and at the distal end 414. This tapering or sloping allows for easier insertion and retraction of instruments in the instrument portion 418. The delivery device portion 416 is configured to receive a delivery device (e.g., endoscope) and the instrument portion 418 is configured to receive an instrument. The instrument portion 418 may have a smaller diameter than a diameter of the delivery device portion 416. The delivery device portion 416 may be coaxial with the elongate braid 400. A ring 424 may extend from the delivery device portion 416 and may be substantially coaxial with the delivery device portion 416. The ring 424 may hold the distal end 404 to the delivery device and may provide a blunt tip geometry that may help to reduce trauma to the patient. The elongate braid 400 may extend fully or partially through the elongate member 410 to the ring 424, and may be fully or partially integrated with the elongate member 410. A clip 420 at the proximal end of the elongate braid 400 may be configured to secure a wall of the elongate braid 400 against a delivery device. Marking bands 408 may be disposed on the elongate braid 408. The marking bands 408 may be radiopaque or a distinctive color such that they are visible to a medical professional while being inserted or inside a body lumen. The marking bands 408 may be, e.g., pad printed, laser etched, etc. on the elongate braid 400. The marking bands 408 may be inside and/or outside of the patient to provide guidance with respect to insertion and advancement/retraction feedback to the medical professional, e.g., in performing cryo-ablation therapies using the radial spray or end spray catheters in conjunction with an endoscope.

Figures 5, 5A:
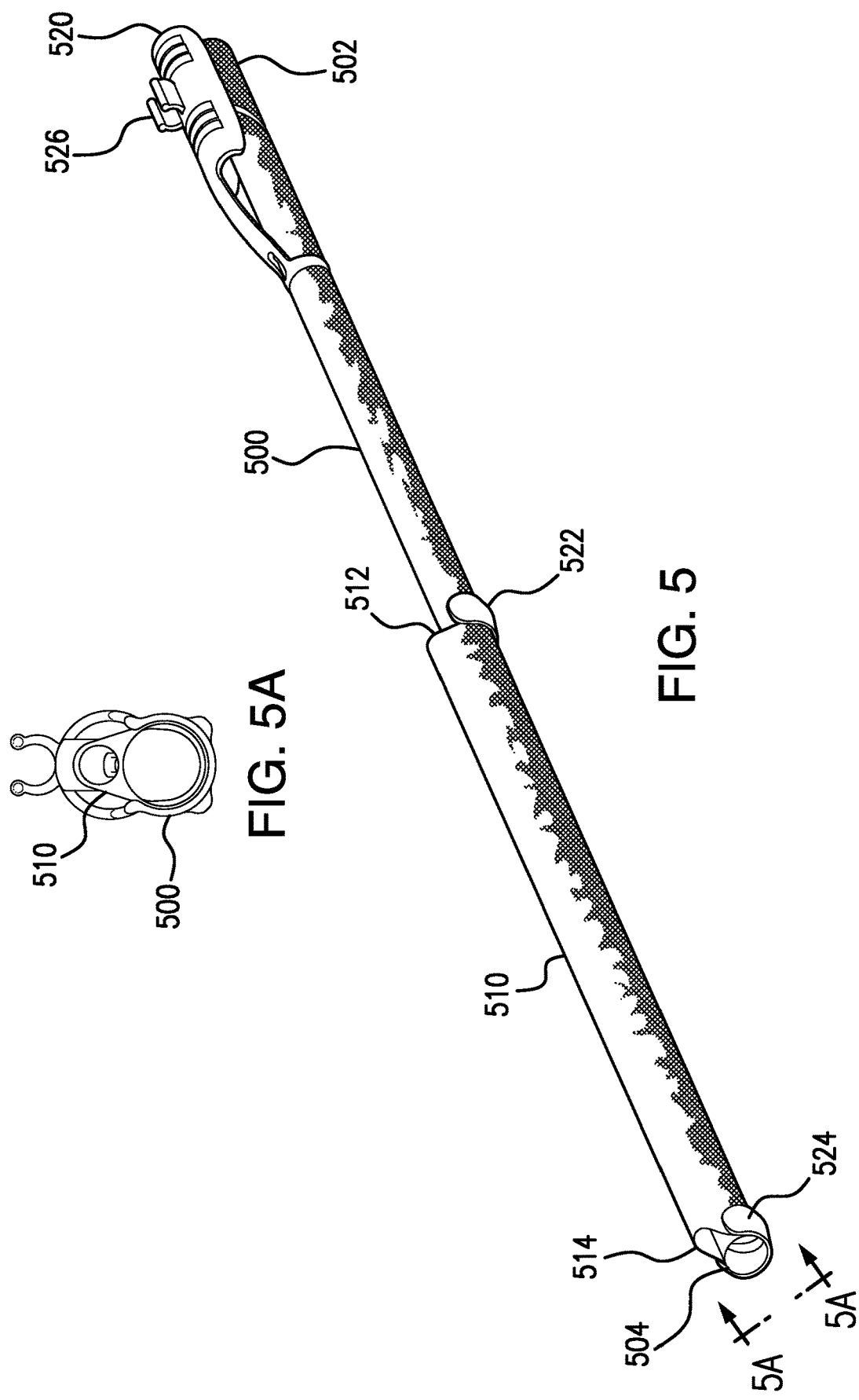
FIGS. 5 and 5A illustrate a perspective and end cross-section view of an instrument guide in accordance with an embodiment of the present disclosure.

With reference to FIG. 5, an embodiment of an instrument guide for a delivery device according to the present disclosure is illustrated, which includes a first clip 520 at the proximal end 502 of the collapsible elongate braid 500 is configured to secure a wall of the elongate braid 500 against a delivery device. The first clip 520 may have a substantially C-shaped channel disposed about the lumen of the elongate braid 500 at the proximal end 512 of the lumen of the collapsible instrument braid 510. The first clip 520 may have a portion raised off and radially away from the elongate braid 500 in an unsnapped configuration. While the first clip 520 is in the unsnapped configuration, the elongate braid 500 may be translated axially in the proximal and distal direction. With the first clip 520 clipped about the elongate braid 500 and an endoscope in a snapped configuration, the elongate braid may be substantially fixed to the endoscope. A second clip 524 may have a substantially C-shaped channel disposed about the lumen of the elongate braid 500 at the distal end 514 of the lumen of the instrument braid 510. The first clip 520 may engage the lumen of the elongate braid 500 about 180 degrees opposed to the second clip 524. A third clip 522 may have a substantially C-shaped channel disposed about the lumen of the elongate braid 500 at the proximal end 512 of the lumen of the instrument braid 510. The second clip 522 and third clip 524 may hold the elongate braid against a delivery device and may keep the proximal end 512 and the distal end 514 radially aligned with each other. Similar clips may be used with other embodiments described herein and otherwise within the scope of the disclosure.

Figure 6:
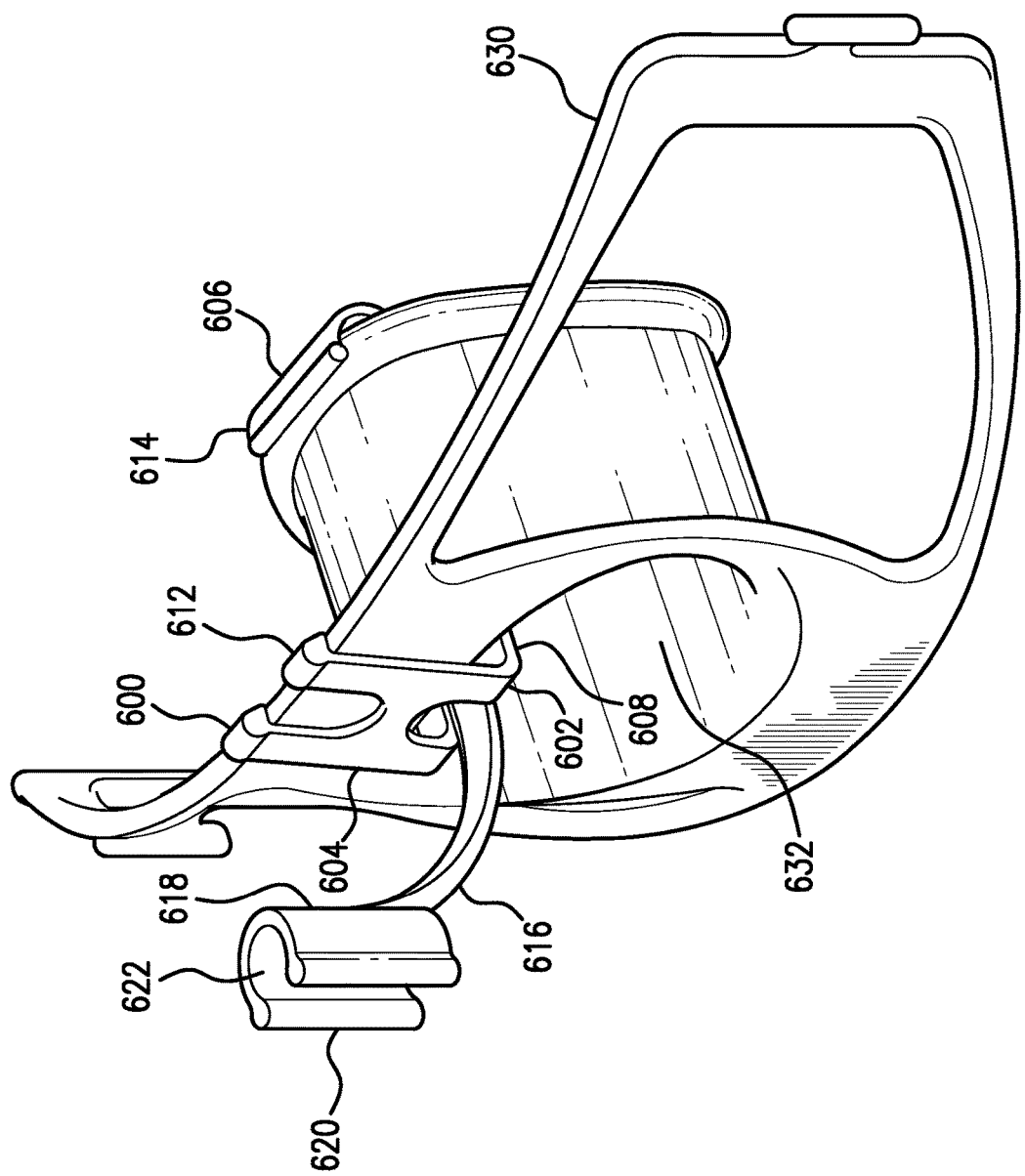
FIG. 6 illustrates an instrument guide accessory in accordance with an embodiment of the present disclosure.

In one embodiment of an instrument guide system including an instrument guide according to one or more of the above embodiments, a mouthpiece, and an accessory device for the external guide that is attachable to the mouthpiece, as illustrated in FIG. 6, an instrument guide accessory 600 has a base 602 having a first end 604, a second end 606, and a base end 608 extending between the first end 604 and the second end 606. The base 602 is configured to span a depth of the mouthpiece 630 (e.g., a bite block). The mouthpiece 630 or bite block, e.g., is placed into the mouth of a patient and includes an opening through which an endoscope or other delivery device, alone or within an instrument guide, may be passed and protected against the patient biting down and damaging the endoscope or other delivery device and/or an instrument that may extended alongside the delivery device, or damaging the instrument guide, if the endoscope and instrument are contained within an instrument guide that extends all the way out through the mouthpiece 630. A first connection element 612 is at the first end 604 of the base 602 and is configured to connect to the mouthpiece 630. A second connection element 614 is at the second end 606 substantially opposing the first connection element 612 and is configured to connect to the mouthpiece 630. The first connection element 612 and second connection element 614 may hook and/or snap the base 602 onto the mouth piece 630. An arm 616 is connected to the base 602 at the base end 608. The arm 616 extends away from the base 602 to a terminal clip end 618. A clip 620 is at the terminal clip end 618 that has a channel 622 along a longitudinal axis configured to receive an instrument. The clip 620 is substantially C-shaped. An instrument may be snapped into the channel 622. Once the instrument is in position inside the patient and no further movement of the instrument is desired, the instrument may be temporarily anchored into the clip 620. The instrument may also be held at a point along its distal portion within the patient by an instrument braid lumen of an external guide that is received along the length of a delivery device. In such cases, the overall length of the external guide could be much shorter than the instrument guide of other embodiments where the instrument guide extends proximally to a point outside of the patient. The instrument may stay fixed relative to the anatomy, while the delivery device and/or catheter is able to be advanced and retracted freely. The longitudinal axis of the channel 622 is substantially perpendicular to an airway path 632 of the mouthpiece 630 and configured to fixedly receive one or more instruments disposed within a braided instrument lumen of an external guide. The arm 616 curves away from the airway path 632 from the base end 608 to the terminal clip end 618. The terminal clip end 618 is configured to fixedly receive one or more instruments with respect to the external guide and independent of relative translation of a delivery device and device within, such as a cryogen delivery catheter within an endoscope. The channel 622 is configured to orient the instrument out and away from the airway path 632 such that it does not obstruct the airway path 632 into the patient and/or does not get in the way of other instruments.

Figure 7:
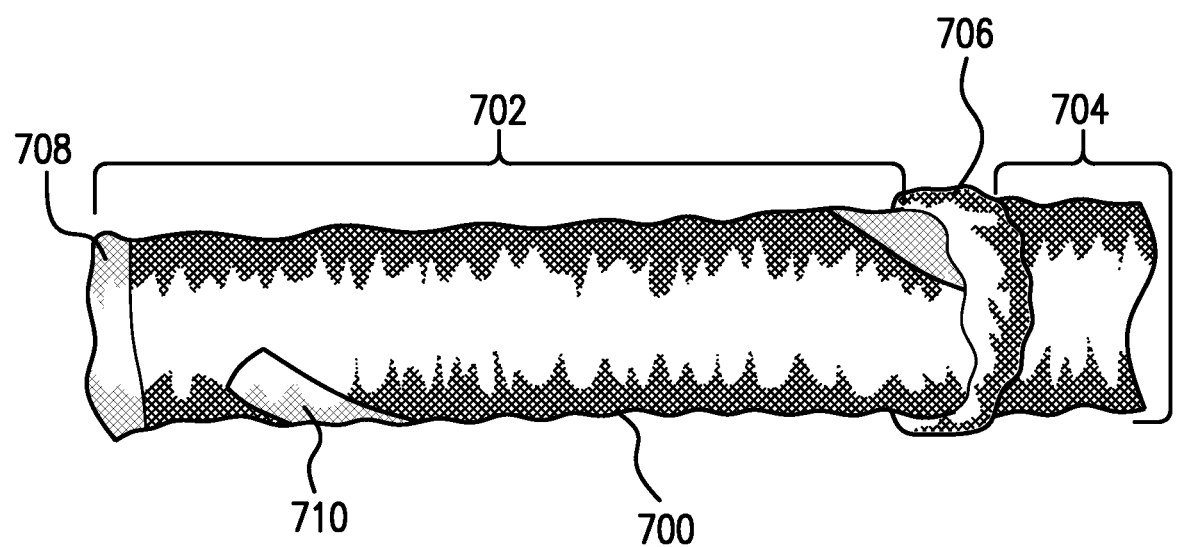
FIG. 7 illustrates an end portion and a mid-portion of an instrument guide in accordance with an embodiment of the present disclosure.

In one embodiment of an instrument guide for a delivery device, as illustrated in FIG. 7, a transitional braid band 706 that is circumferential about the collapsible elongate braid 700, separates an end portion 702 of the elongate braid 700 from a mid-portion 704 of the elongate braid 700. The proximal end opening of the elongate braid or the distal end opening of the elongate braid 700, or both, have a tip coating 708 that may be a thermoplastic elastomer. An end coating 710 may be disposed within a lumen of the elongate braid 700 along the end portion 702. The end coating 710 may be helical about the elongate braid 700. The tip coating 708 and/or end coating 710 may have a higher friction coefficient than that of the elongate braid 700. The coating(s) may have traction with a delivery device within the lumen of the elongate braid 700. During rotation/torsion of the delivery device and/or the elongate braid 700, the coating(s) may maintain the elongate braid 700 in substantially the same radial position with respect to the delivery device, while still allowing the delivery device to inserted into and retracted from the elongate braid when the delivery device is loaded into or removed from the instrument guide. The end portion 702 may be compressed longitudinally to more easily receive insertion of a delivery device into the lumen of the elongate braid 700. The transitional braid 706 prevents the mid-portion 704 of the elongate braid 700 from compressing in the longitudinal direction during this initial insertion of the delivery device. Similar coatings, locations, braids, and materials may be used with other embodiments described herein and otherwise within the scope of the disclosure.

In various of the embodiments described here or otherwise within the scope of the present disclosure, one or more openings at ends of the instrument braid and/or elongate braid may be created by inserting a tapered tip mandrel through the braid and expanding the filaments (e.g., strands or wires) of the braid such that the filaments conform to and settle around the mandrel's outer diameter. This process may preserve the continuity of the woven material of the instrument braid and/or elongate braid, while allowing the formation of the one or more end openings. With one end of a braid worked into an opening via the mandrel, the mandrel may then be advanced through the braid to an additional end of the elongate braid or instrument braid to create a second opening. One or more end openings of the instrument braid and/or the elongate braid may be folded into circumferential z-fold pleats that are maintained via heat-setting, a gel, an adhesive, or the like. Such pleats may allow the braid to efficiently attain a low profile when there is no instrument passing through the lumen of the braid. Alternatively, the elongate braid and instrument braid sections may be created by integrating a braided, extruded, cast, or molded instrument braid section with a separate braided, extruded, cast or molded elongate member. One or more end openings and/or braids may be created by techniques described herein or as otherwise known.

A medical professional may use the various embodiments of instrument guide of this disclosure in a body lumen of a patient according to various methods. For example, a medical professional may insert a delivery device into a collapsible elongate braid of instrument guide. An instrument may be inserted into a collapsible instrument braid of the instrument guide. The elongate braid may be clipped to the delivery device, fixing the rotational and longitudinal position of the instrument guide with respect to the delivery device once a desired orientation and location are reached. The instrument guide may be inserted into a patient. The instrument may be translated proximally/distally independent of the delivery device and/or a device inserted within the delivery device and then clipped in a fixed position when desired. Once fixed in the clips, the delivery device, instrument guide, and instrument may be rotated and/or translated such that the instrument guide holds the instrument in the same radial position with respect to the delivery device.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the spirit and scope of the disclosure. All such similar substitutes and modifications apparent to those skilled in the art are deemed to be within the spirit and scope of the disclosure as defined by the appended claims.

What is claimed is:

1. An instrument guide, comprising:
   a collapsible elongate braid with a proximal end opening, a distal end opening, and a lumen extending therebetween configured to slidingly receive a delivery device;
   a collapsible instrument braid with a proximal end opening, a distal end opening, and a lumen extending therebetween configured to slidingly receive an instrument,
   wherein the instrument braid lumen extends substantially parallel to the elongate braid lumen; and
   a first clip having a substantially C-shaped channel disposed about the lumen of the elongate braid at the proximal end opening of the lumen of the instrument braid and a second clip having a substantially C-shaped channel disposed about the lumen of the elongate braid at the distal end opening of the lumen of the instrument braid.

2. The instrument guide of claim 1, wherein the instrument braid is braided with the elongate braid.

3. The instrument guide of claim 1, further comprising a coating disposed within the lumen of the elongate braid adjacent to the instrument braid, the coating having a higher coefficient of friction than the elongate braid.

4. The instrument guide of claim 3, wherein the coating is disposed proximal to the proximal end opening of the instrument braid and distal to the distal end opening of the instrument braid.

5. The instrument guide of claim 1, further comprising reinforcing braided rings disposed at and extending around each of the proximal end openings and the distal end openings of the instrument braid and the elongate braid.

6. The instrument guide of claim 5, wherein the rings are braided with the proximal end opening and the distal end opening.

7. The instrument guide of claim 1, further comprising a clip distal to the proximal end opening of the elongate braid that is configured to axially and rotationally fix the instrument guide with respect to a delivery device received within the elongate braid.

8. The instrument guide of claim 1, wherein the elongate braid has a length and a midpoint along the length, and the instrument braid has a length with the proximal end opening of the instrument braid beginning at substantially the midpoint of the elongate braid and extending along the lengths of the elongate braid and instrument braid to the distal end opening of the instrument braid coterminous with the distal end opening of the elongate braid.

9. The instrument guide of claim 1, wherein the distal and proximal end openings of the lumen of the instrument braid are sloped.

10. The instrument guide of claim 1, further comprising a transitional braid band that extends circumferentially about the elongate braid, separating a distal portion of the elongate braid from a mid-portion of the elongate braid.

* * * * *